US00PP18787P3

(12) United States Plant Patent
Mawley et al.

(10) Patent No.: US PP18,787 P3
(45) Date of Patent: May 6, 2008

(54) APPLE TREE NAMED 'LADY IN RED'

(50) Latin Name: ***Malus* Pumila Mil**
Varietal Denomination: Lady in Red

(75) Inventors: Robert Basil Mawley, Havelock North (NZ); Elaine Florence Mawley, Havelock North (NZ)

(73) Assignee: RB and EF Mawley Family Trust (NZ)

( * ) Notice: Subject to any disclaimer, the term of this patent is extended or adjusted under 35 U.S.C. 154(b) by 0 days.

(21) Appl. No.: 11/445,033

(22) Filed: May 31, 2006

(65) Prior Publication Data

US 2007/0283465 P1 Dec. 6, 2007

(51) Int. Cl.
*A01H 5/00* (2006.01)

(52) U.S. Cl. ..... Plt./161

(58) Field of Classification Search ..... Plt./161, Plt./172
See application file for complete search history.

*Primary Examiner*—Kent Bell
(74) *Attorney, Agent, or Firm*—Wells St John P.S.

(57) ABSTRACT

A new and distinct variety of apple tree is described and which produces a highly colored red fruit which is mature for harvesting and shipment about one week earlier than the Cripps Pink cultivar (U.S. Plant Pat. No. 7,880) when grown under the ecological conditions prevailing near Hawkes Bay, New Zealand.

6 Drawing Sheets

BACKGROUND OF THE NEW VARIETY

The present invention relates to a new, novel and distinct variety of apple tree '*Malus* Pumila' Mil which has been denominated varietally as 'Lady in Red,' and more specifically to a novel apple tree which produces fruit having a rather intense red coloration and an earlier harvesting date than the variety which it is most closely similar to.

ORIGIN AND ASEXUAL REPRODUCTION

The present apple tree variety was discovered by the inventors as a chance, limb mutation of a 'Cripps Pink' apple tree (U.S. Plant Pat. No. 7,880) during the 1996 growing season at their orchard which is located in Hawkes Bay, New Zealand. The tree upon which the mutation was discovered was then growing on 'M26' rootstock (unpatented) and which is a common rootstock for apple trees. The above identified tree was growing within the cultivated area of the inventors' orchard which was then located at Te Mata-Mangateretere Road, Hawkes Bay, New Zealand. The original mutation was discovered within a block of 'Cripps Pink' apple trees which had been established following the original release of the 'Cripps Pink' apple tree variety in the country of New Zealand.

The new and novel variety was originally identified due to its production of fruit having an earlier harvesting date, and much brighter red fruit coloration. In this regard, the fruit on the mutated limb appeared to be consistently ahead of the color development of fruit on other bearing limbs of the 'Cripps Pink' apple tree when growing in the same block of trees. This color development was particularly notable inasmuch as the fruit produced by the 'Cripps Pink' apple tree, U.S. Plant Pat. No. 7,880 typically occurs later in the season. In relative comparison to the 'Cripps Pink' apple trees growing in the same geographical vicinity, the present variety is distinguishable therefrom by producing a highly colored fruit and further is ripe for harvesting and shipment at least one week earlier at the same geographical location in New Zealand.

Bud wood was taken from the original chance mutated limb in 1996 and was subsequently grafted into six trees which were then growing in the orchard of the inventors' and which were established on 'M26' rootstock (unpatented). These asexual reproduced trees produced their first crop during the autumn of 1999. These first asexually reproduced trees and the fruit produced thereby were again reviewed studied and compared to the original mutated limb and it was determined that the fruit produced by these asexually reproduced trees remained true to that found in the original mutated limb. Thereafter, the inventors asexually reproduced 68 additional trees that were planted for further evaluation. The fruit and these trees have been continually observed and it has been determined that these repropagated trees are true to the characteristics of the original chance mutated limb in all observable aspects.

The present variety was the subject of a PVR application in New Zealand, (Application No. APP 142) and which was filed on Aug. 31, 1998, and which was granted as PVR No. 2377 on Jun. 9, 2005. The inventors have made no use of the present variety which is inconsistent with the provisions of 35 U.S.C. § 102, nor have they distributed any reproducible plant parts of the new variety to any third party as of the filing date of the present U.S. Plant Patent Application.

SUMMARY OF THE VARIETY

The 'Lady in Red' apple tree is characterized as to novelty and is otherwise noteworthy and distinguishable from the 'Cripps Pink' cultivar U.S. Plant Pat. No. 7,880 by producing an apple which, at harvest maturity, has a brighter, more intense red coloration, and which further develops this same red coloration much earlier in the growing season when compared with the fruit produced by the 'Cripps Pink' cultivar. Still further, the present variety has a relatively early harvesting date of about 10 April to about 30 April under the ecological conditions occurring in Hawkes Bay, New Zealand. This date of harvesting is approximately one week earlier then the 'Cripps Pink' cultivar growing in the same geographical location. In addition to the forgoing, the present variety develops sufficient color for harvesting and shipment such that approximately 70% of the fruit is harvested during the first pick, with the remaining 30% is harvested during a second pick.

BRIEF DESCRIPTION OF THE DRAWINGS

The accompanying drawings are color photographs of various aspects of the new variety of apple tree. The colors as shown herein are as nearly true as is reasonably possible for color representations of this type. Due to chemical development, processing and printing, the leaves and fruit of the present tree may or may not be accurate when compared to the actual specimen. For this reason, future color references should be made to the color plates as provided by The Royal Horticultural Society Color Chart, 2001 Edition and other general color descriptions as provided hereinafter.

DETAILED DESCRIPTION

Figure 1:
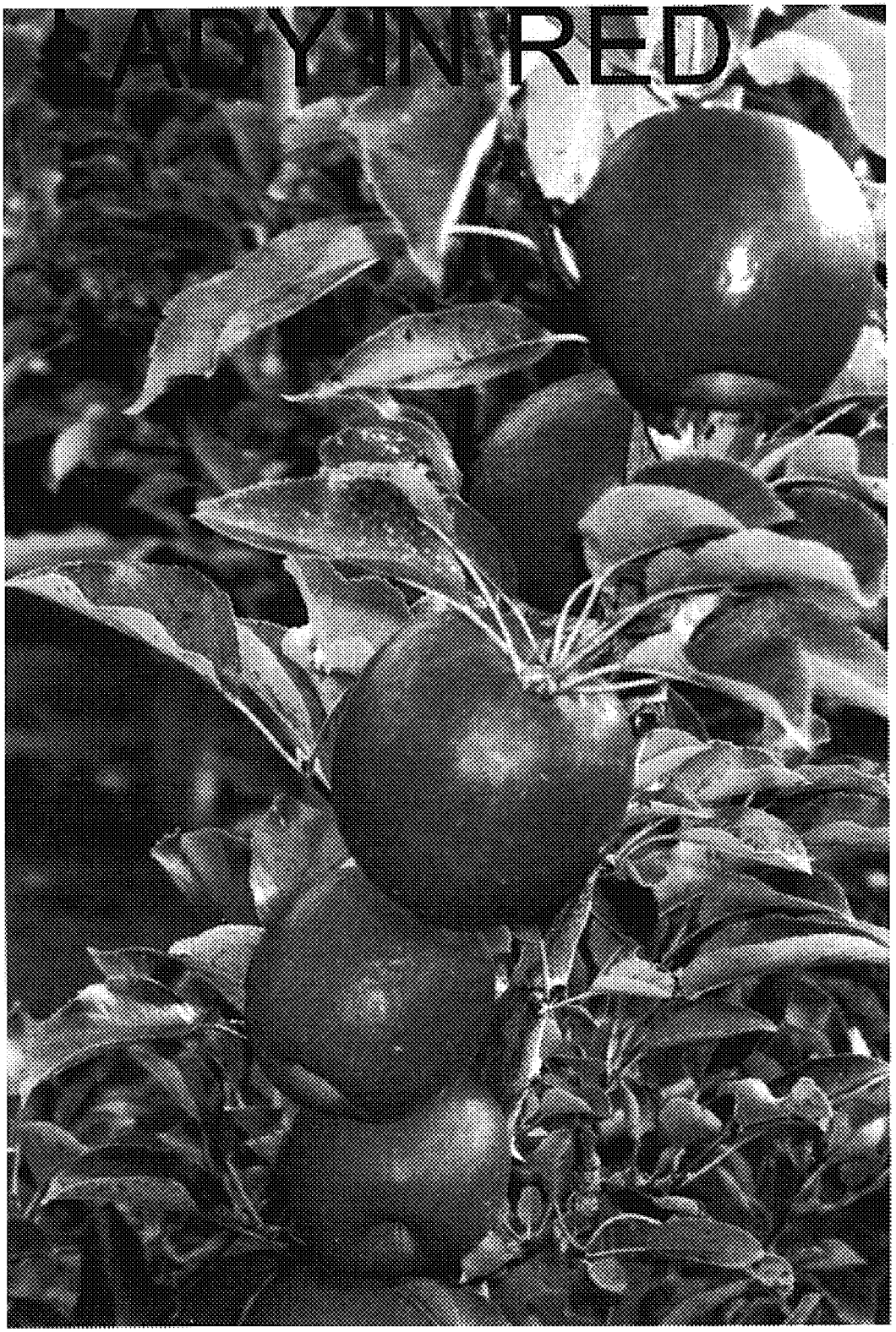
FIG. 1 illustrates the growing habit of the new variety 'Lady in Red' as seen on the original limb mutation which was discovered in the orchard of origin.
Figure 2:
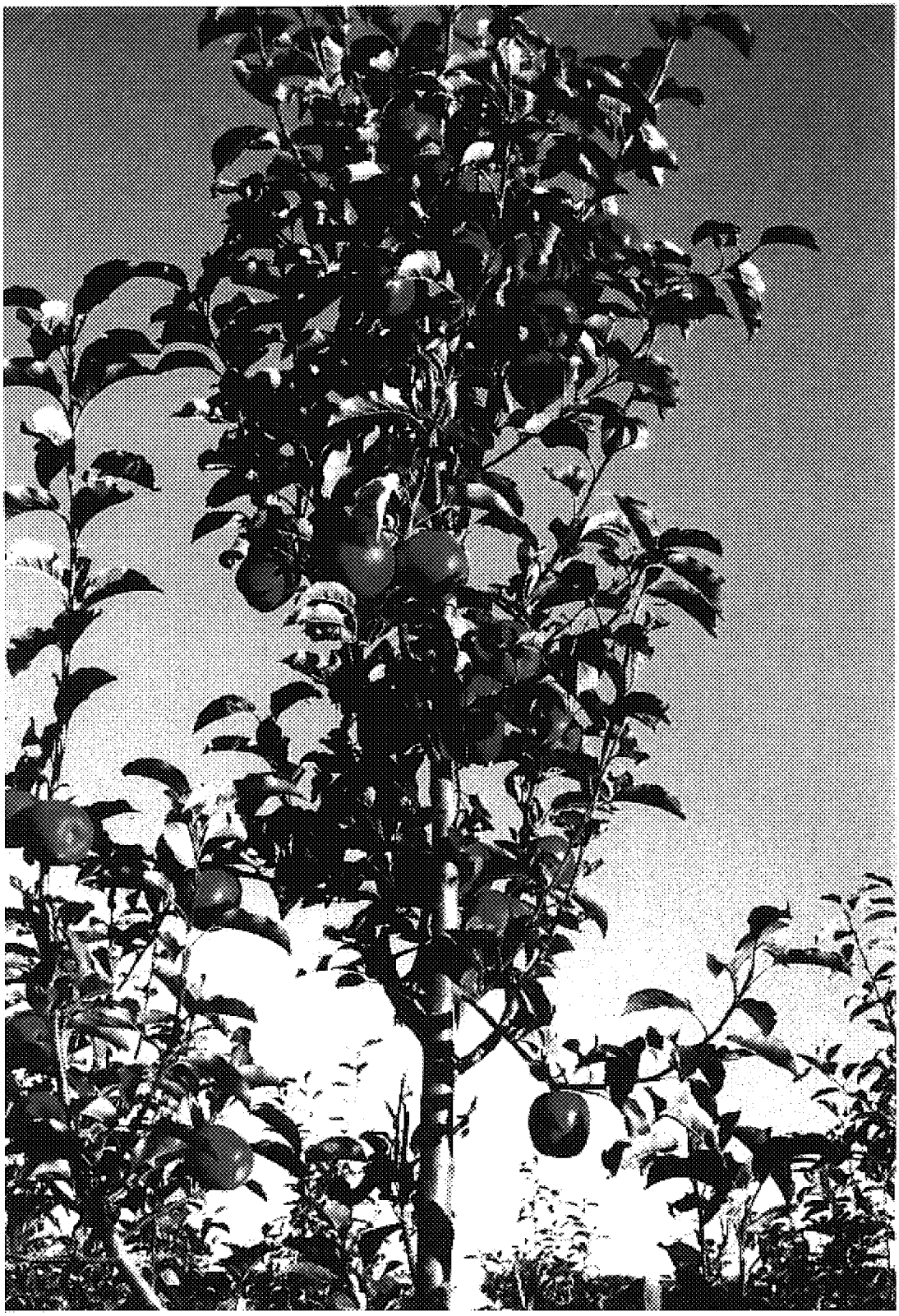
FIG. 2 is a second view of the original limb mutation showing the growing habit of the new variety.
Figure 3:
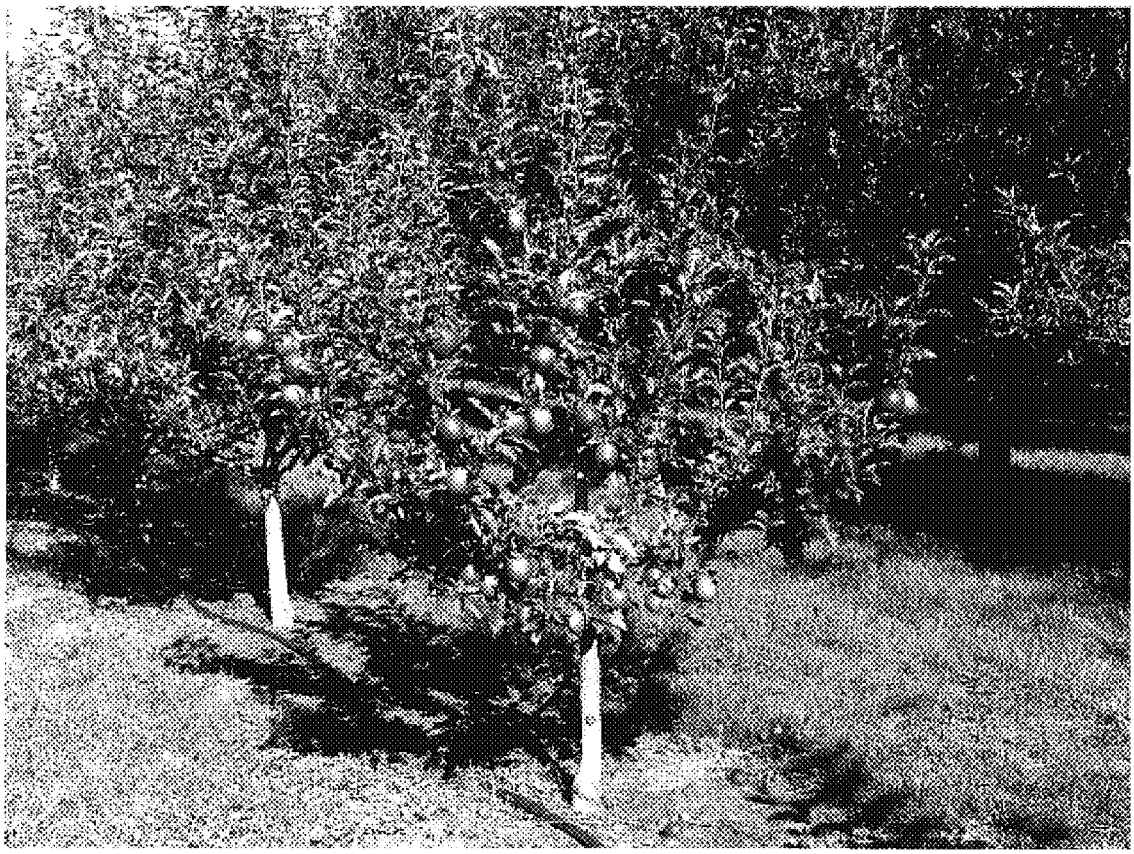
FIG. 3 is view of a third generation, asexually reproduced tree of the present variety showing the foliage and typical branching development of the present variety.
Figure 4:
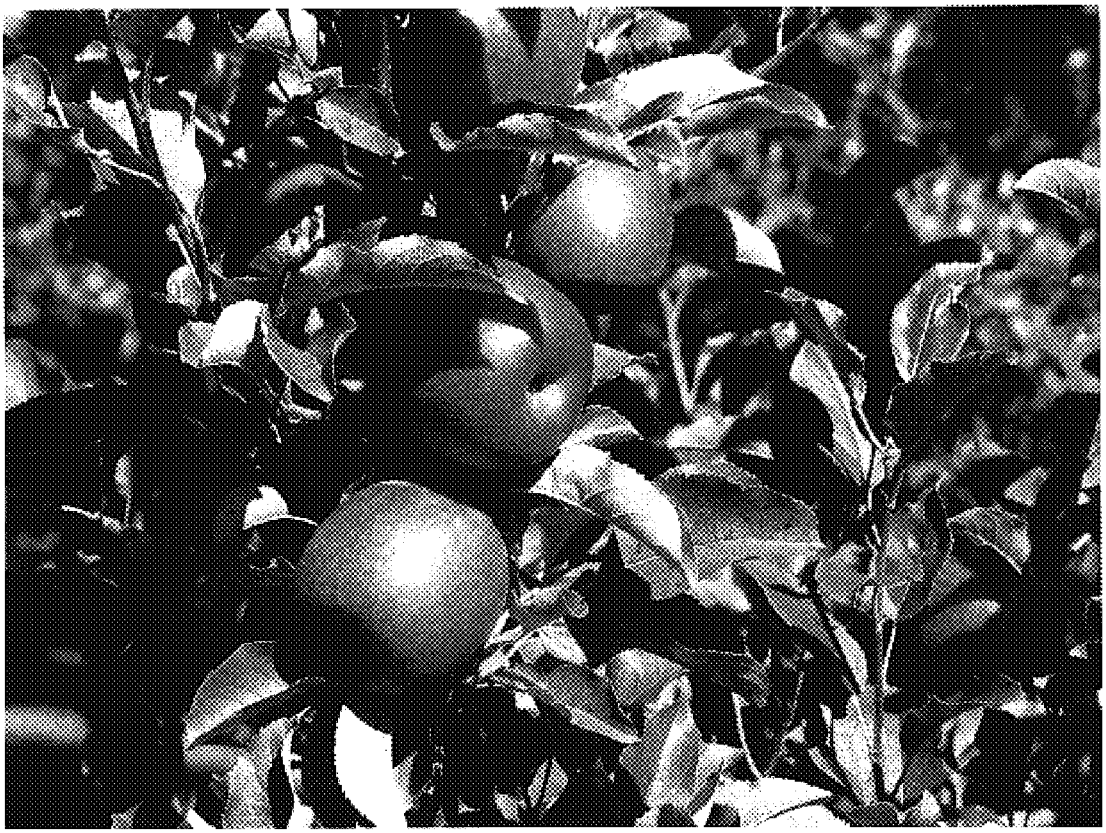
FIG. 4 illustrates a first view of fruit growing on a third generation tree as it approaches harvest maturity.
Figure 5:
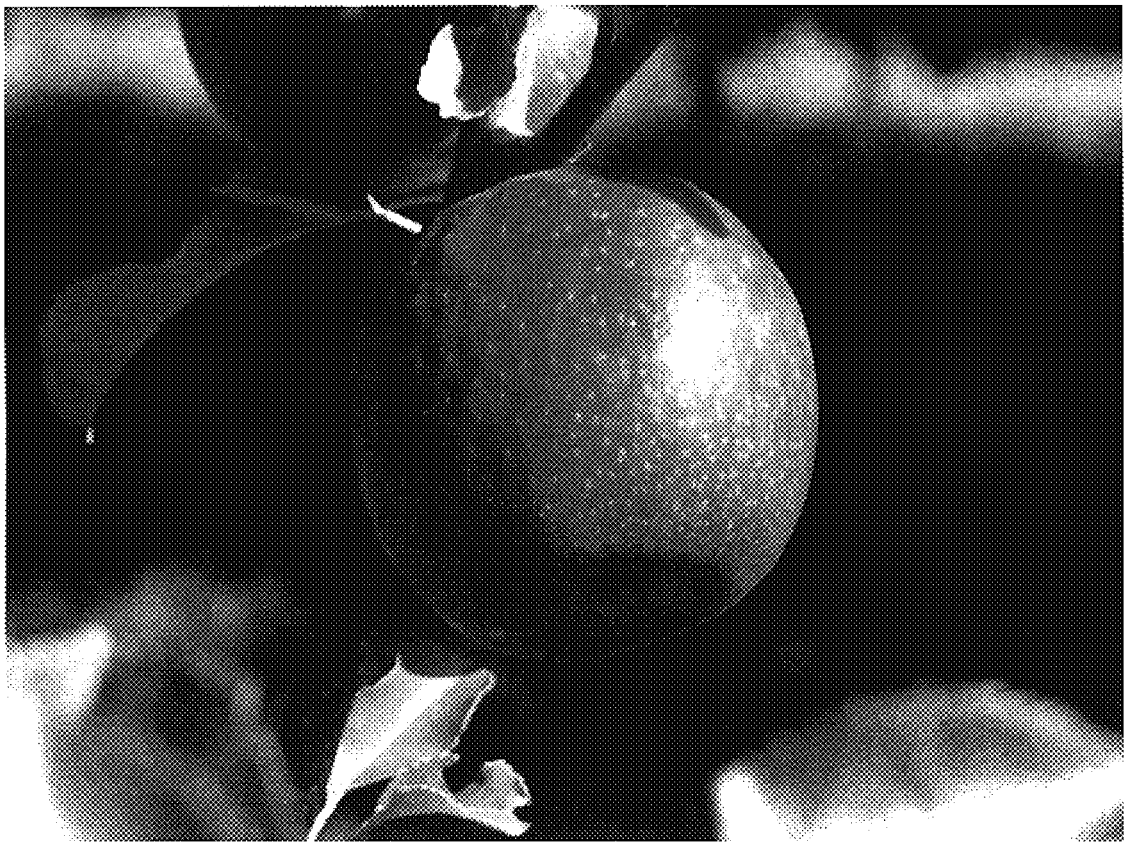
FIG. 5 illustrates a second more close-up view of a single fruit growing on a third generation tree.
Figure 6:
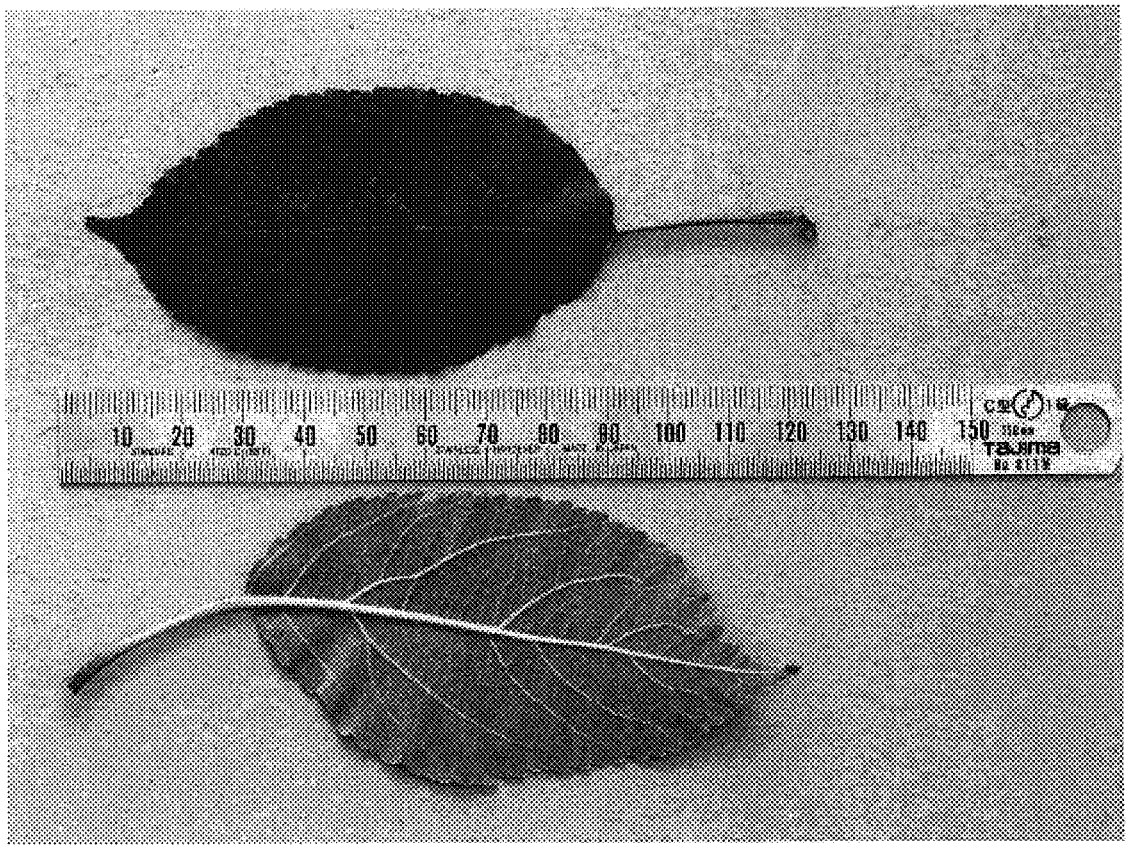
FIG. 6 shows the dorsal and ventral coloration of mature leaves taken from a third generation tree.

Referring more specifically to the pomological details of this new and distinct variety of apple tree, the following has been observed relative to 6 year old trees during the 2005-2006 growing season under the ecological conditions prevailing in the orchard of origin which is located near Hawkes Bay, New Zealand. All major color code designations are by reference to The Royal Horticultural Society Color Charts, 2001 Edition. Common color names are also used occasionally.

Tree:

*Size.*—Generally — Medium to large as compared to other common varieties. Six year old trees have a height of about 3 meters, and a spread of about 2 meters.

*Growing habit.*—Considered upright to slightly spreading.

*Fruit bearing.*—Fruit appears on both one year old and older spurs.

*Vigor.*—Considered vigorous when grown on 'M9' rootstock (unpatented).

Trunk:

*Size.*—On trees that are six years old and which are growing on 'M9' rootstock, the tree circumference when measured at a height of 500 mm, above ground level was about 210 mm.

*Trunk bark color.*—Generally — Gray-green (RHSCC 196D).

Branches:

*Branches.*—Surface texture — Considered smooth.

*Branch bark color.*—Considered gray-green (RHSCC 196D) at commercial maturity.

*Branching habit.*—Generally — Considered moderate for the species.

*Crotch angle.*—Generally — Typically 40 degrees when measured from the horizontal plane.

*Growth habit.*—Spurs — As a general matter, approximately 3.3 spurs occur per 100 mm. of new growth on 2 year old and older wood.

*Annual growth.*—Length — Approximately 580-760 mm. when measured on extension shoots arising from branches which are located approximately 1.5 meters above ground level.

*Internode length.*—One year old shoots — Approximately 25 to 36 mm. in length, and having a thickness of about 26 to 29 mm. when measured at the center of the middle internode.

*Pubescence.*—Present and considered moderate.

*Bark lenticels.*—Size — Considered average for the variety, about 0.93 mm. in diameter.

*Bark lenticels.*—Numbers — Considered numerous.

Leaves:

*Average leaf length.*—About 86.7 mm.

*Average leaf width.*—Approximately 50.1 mm.

*Average length to width ratio.*—About 1.73 mm.

*Position of leaf.*—Considered upward posed.

*Marginal form.*—Considered serrate.

*Dorsal surface texture.*—Considered glabrous and glossy.

*Ventral surface texture.*—Slightly pubescent.

*Petiole length.*—Generally speaking it is considered average, about 26.9 mm.

*Leaf color.*—Dorsal surface — Green, (RHSCC 147A); Leaf Shape — Generally elliptical; Leaf Apex — Shape — narrowly acute; Leaf Base — Shape — arculate.

Flowers:

*Bloom period.*—Generally speaking, the present variety blooms approximately mid-October under the ecological conditions prevailing in Hawkes Bay, New Zealand. This bloom period is approximately 3 weeks long.

*Flower petals.*—Size — Considered large for the species.

*Flower petals.*—Numbers — 5.

*Flower petal arrangement.*—The flower petals of the present variety touch adjacent flower petals.

*Flower buds.*—Color — Red-purple, (RHSCC 69C). The flower bud color fades with increasing senescence to white as the flower opens. Vegetative buds — Shape — Deltoid-ovate, Vegetative Buds — Length — about 3.18 mm. Vegetative Buds — Width — about 3.18 mm. when measured at the base. Floral Buds — Shape — Ovate to oblong. Floral Buds — Length — On average about 18.36 mm. Floral Buds — Width — about 5.02 mm. when measured at the widest point.

*Sepals.*—Small for the species.

*Sepals.*—Shape — Pointed.

*Sepals.*—Color — Green and having a red tip. These colors are not particularly distinctive of the variety, however.

*Ovary.*—Surface texture — Considered pubescent.

Fruit:

Maturity when described.—Ripe for commercial harvesting and shipment about 10 April to about 30 April under the ecological conditions prevailing near Hawkes Bay, New Zealand.

*Average size.*—Considered large for the species.

*Average width.*—Approximately 75 mm.

*Average height.*—Approximately 69.2 mm.

*Average fruit weight.*—Approximately 252.3 grams. Fruit weight is always contingent upon prevailing cultural practices, and therefore this feature of the present variety cannot be considered a distinctive characteristic thereof.

*Fruit shape.*—Considered oblong and weakly crowning at the distal end thereof. The present variety is symmetrical when viewed from the side, and further strong ribbing is evident.

*Stem cavity.*—Width — Approximately 37.8 mm.

*Stem cavity.*—Depth — Considered average to deep for the variety, about 22.3 mm. Fruit stem — Color — The region exposed to sunlight is grey-red (RHSCC 108B), however regions which are shaded are yellow-green (RHSCC 153B).

*Eye.*—Considered average for the species and further having a partly open aperture.

*Eye basin.*—Width — Considered medium to broad, approximately 34.9 mm.

*Eye basin.*—Depth — Considered medium to deep, about 11.7 mm.

*Fruit stem.*—Thickness — About 2 to about 2.5 mm.

*Fruit stem.*—Length — About 15 to about 24 mm.

*Sepals.*—Length — Average and touching, about 4.49 mm.

*Fruit skin.*—Surface texture — Slightly dimpled.

*Bloom.*—Generally speaking it is absent and the fruit skin appears greasy.

*Fruit skin.*—Thickness — Medium for the variety, about 0.0308 mm.

*Tendency to crack.*—Absent.

*Fruit skin color.*—Background — Yellow-Green, (RHSCC 149C).

*Fruit skin color.*—Over color — Approximately 80% of the skin surface has a red coloration (RHSCC 53A).

*Russeting.*—Generally speaking, little or no russeting appears around the stem end and the eye cavities of the present variety.

*Lenticels.*—Size — Considered large for the species and round in shape. Lenticels — Diameter — about 0.83 mm. The lenticels do not appear to extend upwardly relative to the fruit skin surface.

*Flesh firmness.*—Considered very firm of the species, about 8 kg per square cm. at harvest.

*Flesh flavor.*—Considered juicy and crisp. The fruit flavor is considered sweet to acidic and further has a mild aroma.

*Fruit brix.*—On average about 13.4.

*Flesh color.*—White (RHSCC 155C). The fruit flesh browns very slowly when exposed to air.

*Keeping quality.*—Considered excellent.

*Fruit use.*—Considered a dessert apple.

*Sinus.*—Shape — Closed.

Seeds:

*Numbers.*—Typically 8 to about 10 seeds will be found.

*Seed locules.*—Numbers — 5.

*Locule aperture.*—Considered closed. Typically 1 to 2 seeds occur per locule.

*Seeds.*—Size — Considered medium, about 10 mm long; and about 5 mm. wide.

*Seed.*—Color — Gray-Brown, (RHSCC 199D).

*Resistance to insects and diseases.*—No particular susceptibilities were noted. The present variety has not been tested to expose or detect any susceptibility or resistances of any known plant and/or fruit diseases.

NOT A COMMERCIAL WARRANTY

The foregoing detailed description has been prepared solely to comply with the provisions of 35 U.S.C. Section 112, and does not constitute a commercial warranty, either expressed or implied that the present variety will in the future display all the botanical, pomological or other characteristics as set forth herein. Therefore, this disclosure may not be relied upon to support any future legal claims including, but not limited to, breach of warranty of merchantability, or fitness for any particular purpose which is directed in whole or in part to the present variety.

Although the new variety of apple tree possesses the described characteristics when grown under the ecological conditions prevailing near Hawkes Bay, New Zealand, it should be understood that variations of the usual magnitude and characteristics incident to changes and growing conditions, fertilization, pruning, pest control and horticulture management are to be expected.

Having thus described and illustrated our new variety of apple tree, what we claim is new and desire to secure by Plant Letters Patent is:

1. A new and distinct variety of apple tree substantially as illustrated and described which is characterized principally as to novelty by producing a highly colored red fruit which is mature for harvesting and shipment about 10 April to 30 April under the ecological conditions prevailing in Hawkes Bay, New Zealand.

* * * * *